US00PP26360P2

(12) United States Plant Patent
Bernabe

(10) Patent No.: US PP26,360 P2
(45) Date of Patent: Jan. 26, 2016

(54) ***SALVIA* PLANT NAMED 'VIOLIN MUSIC'**

(50) Latin Name: ***Salvia* hybrid**
Varietal Denomination: Violin Music

(71) Applicant: Catherine Bernabe, El Campello (ES)

(72) Inventor: Catherine Bernabe, El Campello (ES)

( * ) Notice: Subject to any disclaimer, the term of this patent is extended or adjusted under 35 U.S.C. 154(b) by 163 days.

(21) Appl. No.: 13/998,083

(22) Filed: Sep. 30, 2013

(51) Int. Cl.
*A01H 5/02* (2006.01)

(52) U.S. Cl.
USPC ..... Plt./475

(58) Field of Classification Search
USPC ..... Plt./475
See application file for complete search history.

(56) References Cited

PUBLICATIONS

Ricanet. Rustica Entretien avec Muriel de Curel, organisatrice de la fete des Plantes de Saint-Jean de Beauregard, retrieved on May 7, 2015, retrieved from the Internet at <http://www.rustica.fr/articles-jardin/entretien-avec-muriel-curel-organisatrice-fete-plantes-saint-jean-beauregard,4795.html> pp. 5-12.*
Ricanet English translation.*
Dossier de presse Fete des Plantes 2011, Le jardin nourricier, nourriture du cops et de l'esprit, retrieved on May 7, 2015, retrieved from the internet at <http://www.journalistes-patrimoine.org/IMG/pdf/Dp_FL11_bd.pdf> pp. 1-8.*
Dossier de presse Google English translation, 2 pp.*
McHutchison Florexpo Unrooted Cuttings 2012-2013, retrieved on May 14, 2015, retrieved from the Internet at <http://mchutchison.com/McH_Florexpo_12-13.pdf> pp. 1-3, 29 and 98-100).*
CNB New Plants catalogue, retrieved on May 7, 2015, retrieved from the Internet at <www.cnb.nl/EN/Pages/Product-Catalog.aspx?ProductId=176> one page.*
New Plants and Flowers Jun. 1, 2012, retrieved on May 19, 2015, retrieved from the Internet at <http://www.newplantsandflowers.com/french-salvia-hybrids-on-dutch-trade-fair/> 2 pp.*

* cited by examiner

*Primary Examiner* — June Hwu
(74) *Attorney, Agent, or Firm* — Penny J. Aguirre

(57) ABSTRACT

A new cultivar of hybrid *Salvia*, 'Violin Music', that is characterized by its flowers that are a bright violet in color, its short plant height with an upright and spreading plant habit, and its black-purple calyces and flowering stems.

2 Drawing Sheets

Botanical classification: *Salvia* hybrid.
Variety denomination: 'Violin Music'.

BACKGROUND OF THE INVENTION

The present invention relates to a new and distinct cultivar of *Salvia* of hybrid origin and will be referred to hereafter by its cultivar name, 'Violin Music'. 'Violin Music' is an herbaceous perennial grown for landscape use.

The new *Salvia* resulted from a controlled breeding program conducted by the Inventor in Henansal, France. The Inventor made crosses in 2008 between unnamed proprietary plants of interspecific hybrid origin (*Salvia chamaedryoides*× *Salvia lycoides*) in the Inventor's breeding program as both the female and male parents. The characteristics of the parents are unknown as seeds where pooled and sown from several crosses. 'Violin Music' was selected as a single unique plant in 2008 from the resulting seedlings of the above crosses.

Asexual propagation of the new cultivar was first accomplished by the Inventor by vegetative stem cuttings in 2009 in Henansal, France. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Violin Music' as a unique cultivar of *Salvia*.

1. 'Violin Music' exhibits flowers that are a bright violet in color.
2. 'Violin Music' exhibits a short plant height and an upright and spreading plant habit.
3. 'Violin Music' exhibits black-purple calyces and flowering stems.

'Violin Music' can be most closely compared to typical plants that are *Salvia microphylla*×*chamaedryoides* hybrids and to *Salvia chamaedryoides* cultivar 'Silver Leaves' (not patented). Typical plant of *Salvia microphylla*×*chamaedryoides* differs from 'Violin Music' in being larger in overall size, in having flowers that are less bright violet, and in having a less spreading plant habit. 'Silver Leaves' differs from 'Violin Music' in having flowers that are dark purple to black in color and in having velvet textured leaves that are silver-gray in color.

BRIEF DESCRIPTION OF THE DRAWING

The accompanying colored photographs illustrate the overall appearance and distinct characteristics of a one year-old plant of the new *Salvia* as grown in a greenhouse in a 15-cm container in Henansal, France.

The photograph in FIG. 1 provides a side view of 'Violin Music' in bloom.

Figure 1:
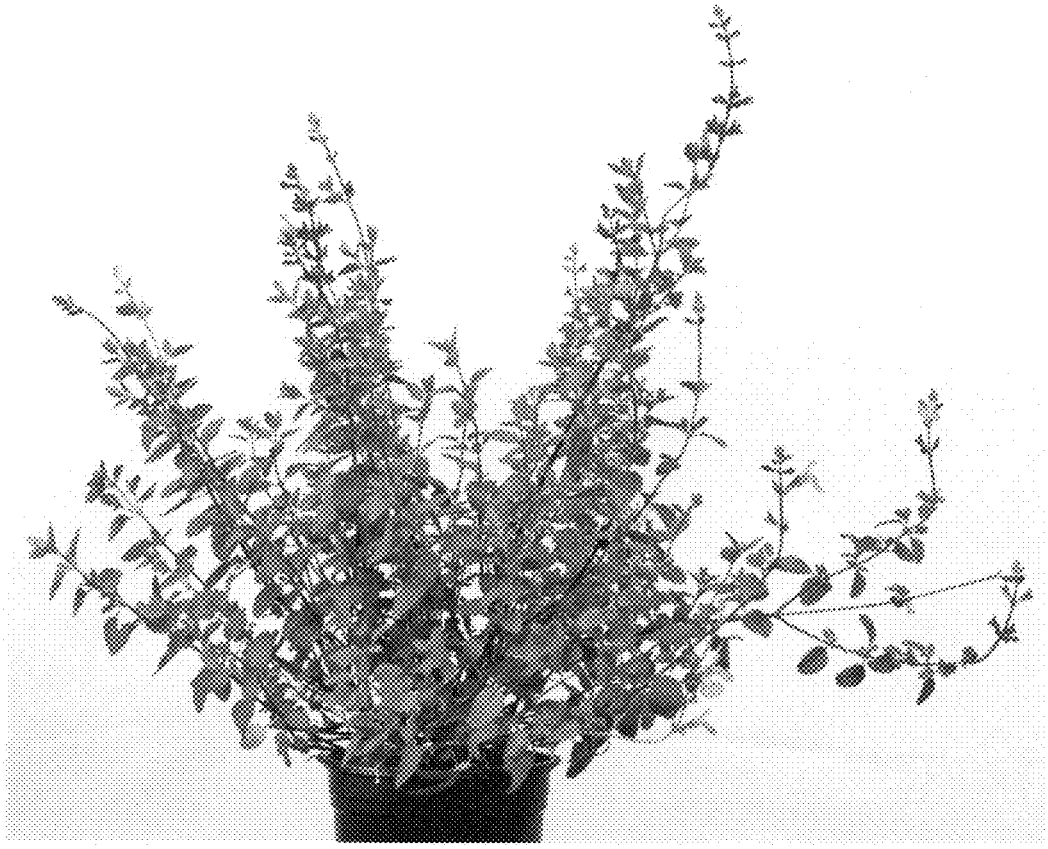
Figure 2:
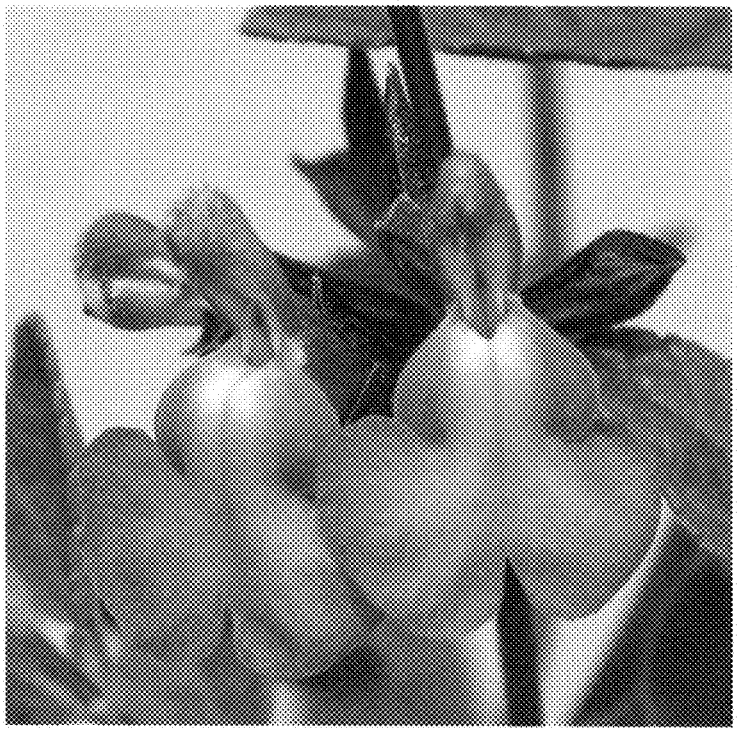

The photograph in FIG. 2 provides a close-up view of the flowers of 'Violin Music'.

Figure 3:
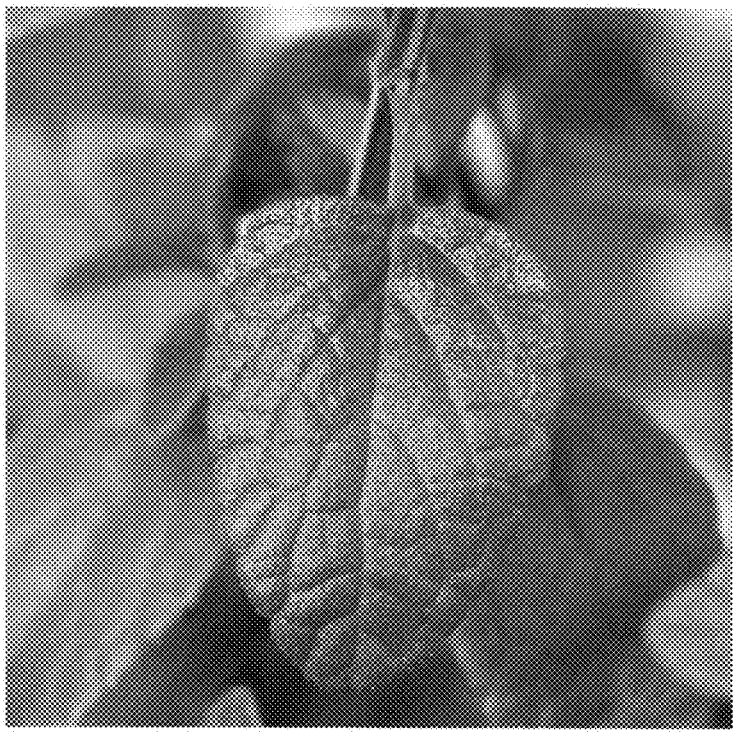

The photograph in FIG. 3 provides a close-up view of a leaf of 'Violin Music'.

The colors in the photographs may differ slightly from the color values cited in the detailed botanical description, which accurately describe the colors of the new *Salvia*.

DETAILED BOTANICAL DESCRIPTION

The following is a detailed description of one year-old plants of 'Violin Music' as grown in a greenhouse in Henansal, France. Plants were grown under average day temperatures ranging from 14° to 30° C. and average night temperatures of 8° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—May to first frost in Henansal, France.

*Plant type.*—Herbaceous perennial.

*Plant habit.*—Broad spreading.

*Plant size.*—Reaches up to 40 cm in height and 70 cm in spread.

*Cold hardiness.*—At least to U.S.D.A. Zone 8.

*Diseases and pests.*—No susceptibility or resistance to diseases or pests have been observed.

*Root description.*—Fibrous, non-spreading.

*Propagation*—Vegetative stem cuttings.

*Growth rate.*—Vigorous.

Stem description:

*Shape.*—Very slightly quadrangular, nearly rounded.

*Stem color.*—Upper surface 183B with base 184C, lower surface 147C.

*Stem size.*—Average of 18.2 cm in length and 2 mm in diameter.

*Stem strength.*—Strong.

*Stem surface.*—Slightly glossy and densely covered with very short soft hairs, average length is 0.2 mm and 157D in color, when rubbed the stems give a "sage" like fragrance.

*Internode length.*—Average of 3.1 cm.

*Branching.*—Average of 10 main stems, an average of 6 lateral braches per main stem.

Foliage description:

*Leaf shape.*—Ovate.

*Leaf division.*—Simple.

*Leaf base.*—Rounded to truncate.

*Leaf apex.*—Obtuse.

*Leaf fragrance.*—When rubbed the leaves give a "sage" like fragrance.

*Leaf venation.*—Pinnate, upper surface is 143B in color, lower surface is 144A in color.

*Leaf margins.*—Slightly crenate and moderately covered with very short glandular hairs; an average of 0.2 mm in length, 157D in color.

*Leaf arrangement.*—Opposite.

*Leaf attachment.*—Petiolate.

*Leaf surface.*—Upper and lower surface very slightly rugose, upper surface slightly glossy and moderately covered with very short glandular hairs an average length of 0.2 mm, 157D in color, lower surface dull.

*Leaf size.*—Up to 2.4 cm in length and 1.7 cm in width.

*Leaf color.*—Young leaves; upper surface 143A, lower surface 143B, mature leaves; upper surface N137B, lower surface 137D.

*Leaf quantity.*—Average of 12 (6 pairs).

*Petioles.*—An average of 1 cm in length and 1 mm in diameter, 143B to 143C in color, surface sparsely covered with short glandular hairs.

Inflorescence description:

*Inflorescence type.*—Terminal verticillaster, individual flowers are in whorls of 6.

*Lastingness of inflorescence.*—Approximately 5 days.

*Inflorescence size.*—An average of 11.9 cm in height and 3.4 cm in width.

*Flower type.*—Labiate.

*Flower number.*—An average of 54 per vertillicaster.

*Flower fragrance.*—None.

*Flower buds.*—Obovate in shape, about 1.1 cm in length and 4 mm in diameter, color; 144C upper side striped 202A with top of immature petals N89A.

*Flower size.*—About 2.3 cm in depth and about 1.5 cm in width (horizontal) and 1.8 cm in height (vertical).

*Peduncle.*—An average of 11.1 cm in length and 1.5 mm in width, held straight on top of lateral branch, strong in strength, color; N186A, surface densely covered with very short soft hairs.

*Pedicels.*—About 4 mm in length and 0.71 mm in diameter, held at an average angle of 20°, strong in strength, N189B in color, surface densely covered with very short soft hairs.

*Calyx.*—Campanulate in shape, average of 1.1 cm in length, 3 mm in width (horizontal) and 6 mm in height (vertical).

*Sepals.*—3, campanulate in arrangement, narrow obovate in shape with lower 70% fused, entire margin, acute apex, cuneate base fused into tube, an average of 1.1 cm in length and 2 mm in width, upper and lower surface is dull and covered with very short glandular hairs, average of 0.1 mm in length and 156D in color, color: immature upper (inner) side; 146C with base 146D, immature lower (outer) side; 144C, upper side striped 202A, top of immature petals N89A, mature upper (inner) side; 146C striped with 146D, mature lower (outer) side; 144C, upper side striped 202A, top of immature petals N89A.

*Petals.*—2, labiate, arranged in 2 lips, lower 65% fused into tube at base, upper and lower lip surface glabrous and dull, upper lip; broad elliptic and folded in shape, entire margin, retuse apex, 2.3 cm in length and 3 mm in width, lower lip; broad spathulate in shape, entire margin with two lobes, retuse apex, 2.8 cm in width and 1.5 mm in length, tube; 1.2 cm in length and 3.5 mm in width, color of upper and lower lips: when opening upper (inner) side; upper lip N87A, lower lip N87B with base N87A, basal spot on lower lip and inside of tube N88D, when opening under (outer) side; upper lip N88D, lower lip N87 with base and tube a blend of N88D and 91C, when fully open upper (inner) side; upper lip N87A, lower lip N87B with base N87A, basal spot on lower lip and inside of tube N88D, when fully open lower (outer) side; upper lip N88D, lower lip N87B with base and tube a blend of N88D and 91C.

Reproductive organs:

*Gynoecium.*—1 pistil, an average of 2.1 cm in length, style is 1.9 cm in length and NN155D in color, stigma is cleft (2 parted) and 90B in color, ovary is 145D in color.

*Androcoecium.*—2 stamens, filaments are NN155D in color and 8 mm in length, anthers are dorsifixed and narrowly elliptic in shape, an average of 1.5 mm in length and N199A in color, pollen is moderate in quantity and 14A.

*Fruit and seed.*—No fruit or seeds detected to date, plants have been observed to be sterile.

It is claimed:

1. A new and distinct cultivar of *Salvia* plant named 'Violin Music' as herein illustrated and described.

* * * * *